United States Patent [19]

McCabe et al.

[11] Patent Number: 5,712,269
[45] Date of Patent: Jan. 27, 1998

[54] $M_2$ RECEPTOR LIGAND FOR THE TREATMENT OF NEUROLOGICAL DISORDERS

[75] Inventors: R. Tyler McCabe, South Salem; Bryan R. Wilson, Tuxedo, both of N.Y.; Christopher A. Rhodes, Stamford, Conn.

[73] Assignee: Pharmaceutical Discovery Corporation, Elmsford, N.Y.

[21] Appl. No.: 377,667

[22] Filed: Jan. 24, 1995

Related U.S. Application Data

[63] Continuation of Ser. No. 42,872, Apr. 5, 1993, abandoned.

[51] Int. Cl.[6] .......................... A61K 31/55; C07D 471/04
[52] U.S. Cl. ............................................. 514/220; 540/495
[58] Field of Search ............................ 540/495; 515/220

[56] References Cited

U.S. PATENT DOCUMENTS 3,406,168   10/1968   Schmidt .................................. 540/495

FOREIGN PATENT DOCUMENTS

| 0 312 895 A2 | 4/1989 | European Pat. Off. | 540/495 |
| 0 344 543 A2 | 12/1989 | European Pat. Off. | 540/495 |
| 0 508 370 A1 | 10/1992 | European Pat. Off. | 540/495 |
| 91/10654 | 7/1991 | WIPO | 540/495 |

OTHER PUBLICATIONS

Engel et al., "Tricyclic Compounds as Selective Muscarinic Receptor Antagonists. 3. Structure–Activity Relationships in a Series of Cardioselective ($M_2$) Antimuscarinics," *J. Med. Chem.*, 32:1718–1724 (1989).

Karton et al., "Synthesis and Biological Activity of Some Methoctramine—Related Tetraamines Bearing a 11–Acetyl-5,11-dihydro-6H-pyrido[2,3-b][1,4]benzodiazepin-6-one Moiety as Antimuscarinics: A Second Generation of Highly Selective $M_2$ Muscarinic Receptor Antagonists," *J. Med. Chem.*, 34:2133–2145 (1991).

Melchiorre et al., "Functionalized Congener Approach to Muscarinic Antagonists: Analogues of Pirenzepine," *J. Med. Chem.*, 36:3734–3737 (1993).

Doods et al., "Therapeutic Potential of CNS–Active $M_2$ Antagonists Novel Structures and Pharmacology," *Life Sciences*, 52:497–503 (1993).

Aubert, I., et al., "Characterization and Autoradiographic Distribution of [$^3$H]AF–DX 384 Binding to Putative Muscarinic $M_2$ Receptors in the Rat Brain," *Eur. J. Pharmacol.* 217(2/3):173–184 (Jul. 7, 1992).

Billard, W., et al., "Characterization of the Binding of $^3$H–SCH 23390, A Selective D–1 Receptor Antagonist Ligand, In Rat Striatum," *Life Sci.* 35(18):1885–1893 (1984).

Bonner, T.I., "The Molecular Basis of Muscarinic Receptor Diversity," *TINS* 12(4):148–151 (1989).

Buckley, N.J., et al., "Localization of a Family of Muscarinic Receptor mRNAs in Rat Brain," *J. Neurosci.* 8(12):4646–4652 (Dec. 1989).

Collerton, D., "Cholinergic Function and Intellectual Decline in Alzheimer's Disease," *Neurosci.* 19(1):1–28 (1986).

Dawson, V.L., et al., "Hippocampal Muscarinic Supersensitivity After AF64A Medial Septal Lesion Excludes $M_1$ Receptors," *Brain Res. Bull.* 25:311–317 (Aug. 1990).

Dawson, V.L., et al., "Alteration in Cortical Muscarinic Receptors Following Cholinotoxin (AF64A) Lesion of the Rat Nucleus *Basalis magnocellularis,*" *Neurobiol. Aging* 13(1):25–32 (1991).

Engel, G., et al., "Evidence for Common Pharmacological Properties of [$^3$H]5-Hydroxytryptamine Binding Sites, Presynaptic 5–Hydroxytryptamine Autoreceptors in CNS and Inhibitory Presynaptic 5–Hydroxytryptamine Receptors on Sympathetic Nerves," *Naunyn Schmiedeberg's Arch. Pharmacol.* 324(2):116–124 (1983).

Engel, W.W., et al., "Tricyclic Compounds as Selective Muscarinic Receptor Antagonists, 3, Structure–Selectivity Relationships in a Series of Cardioselective ($M_2$) Antimuscarinics," *J. Med. Chem.* 32(8):1718–1724 (1989).

Entzeroth, M. and Mayer, N., "Labeling of Rat Heart Muscarinic Receptors Using the New $M_2$ Selective Antagonist [$^3$H]AF–DX 384," *Biochem. Pharmacol.* 40(7):1674–1676 (1990).

Glass, J.D., et al. "Benzyloxycarbonylarginine Nitrophenyl Ester Salts: 1–Hydroxybenzotriazole Catalyzed Acylations of Amines," *Int. J. Peptide Protein Res.* 12(2):75–80 (Aug. 1978).

Goldman, J., et al. "Aging of the Brain: Dementia of the Alzheimer's Type," *Principles of Neural Science*, 3rd Edition, ed. Kandel et al., Chapter 62 (Part X), 974–983 (Elsevier New York 1991).

Greenstein, J.P., et al., "Chemical Procedures for Synthesis of Peptides," *Chemistry of the Amino Acids*, vol. 2, 891–895, John Wiley and Sons, Inc. (New York 1961).

Hammer, R., et al., "Binding Profile of a Novel Cardioselective Muscarine Receptor Antagonist, AF–DX 116, to Membranes of Peripheral Tissues and Brain in the Rat," *Life Sci.* 38(18):1653–1662 (1986).

Hanisch, U.–K., et al., "Modulation of Hippocampal Acetylcholine Release: a Potent Central Action of Interleukin–2," *J. Neurosci.* 13(8):3368–3374 (Aug. 1993).

Lapchak, P.A., et al. "Binding sites for [$^3$H]AF–DX 116 and Effect of AF–DX 116 on Endogenous Acetylcholine Release from Rat Brain Slices," *Brain Res.* 496(1/2):285–294 (Sep. 4, 1989).

Lee, K.S., et al. "1,3–Dipropyl–8–Cyclopentylxanthine (DPCPX) Inhibition of [$^3$H]N–Ethylcarboxamidoadenosine (NECA) Binding Allows the Visualization of Putative Non–A1 Adenosine Receptors," *Brain Res.* 368(2):394–398 (Mar. 19, 1986).

(List continued on next page.)

*Primary Examiner*—Robert T. Bond
*Attorney, Agent, or Firm*—Arnall Golden & Gregory

[57] ABSTRACT

Muscarinic $M_2$ receptor ligands are described which are suitable for the treatment of neurological disorders, and which may be administered with minimal side-effects. A method of synthesis of these compounds is also described.

10 Claims, 7 Drawing Sheets

OTHER PUBLICATIONS

Liao, C.-F., et al. "Molecular Cloning and Expression of a Fifth Muscarinic Acetylcholine Receptor," *J. Biol. Chem.* 264(13):7328–7337 (May 5, 1989).

Lott, R.S., et al., "Trimethylsilyl Iodide as a Peptide Deblocking Agent," *J.C.S. Chem. Commun.* 495–496 (1979).

Lynch, C.J., et al., "Evidence for High and Low Affinity $\alpha_2$–Receptors," *J. Biological Chem.* 256(7):3298–3303 (Apr. 10, 1981).

Martin, B.R., et al., "Relationship of the Biodisposition of the Stereoisomers of Nicotine in the Central Nervous System to Their Pharmacological Actions," *J. Pharmacol. Exper. Therapeu.* 226(1):157–163 (Jul. 1983).

Mash, D.C., et al., "Loss of M2 Muscarine Receptors in the Cerebral Cortex in Alzheimer's Disease and Experimental Cholinergic Denervation," *Science* 288:1115–1117 (May 31, 1985).

McCabe, R.T., et al., "Characterization of Benzodiazepine Receptors with Fluorescent Ligands," *FASEB J.* 4:2934–2940 (Aug. 1990).

Michel, A.D., et al., "Direct Labeling of Rat $M_3$–Muscarinic Receptors by [$^3$H]4DAMP," *Eur. J. Pharmacol.* 166(3):459–466 (Aug. 3, 1989).

Morris, R.G.M., "Spatial Localization Does Not Require Presence of Local Cues," *Learning and Motivation* 12:239–260 (1981).

Pittel, Z., et al., "Distinct Muscarinic Receptor Subtypes Differentially Modulae Acetylcholine Release from Corticocerebral Synaptosomes," *J. Neurochem.* 55(2):665–672 (Aug. 1990).

Quirion, R., et al., "Muscarinic Receptor Subtypes in Human Neurodegenerative Disorders: Focus on Alzheimer's Disease," *TIPS* Suppl. 80–84 (Dec. 1989).

Sakahibara, S., et al., "A New Reagent for the p–Nitrophenylation of Carboxylic Acids," *Bull. Chim. Soc. Jpn.* 37(8):1231–1232 (Aug. 1964).

Sloan, J.W., et al., "The Comparative Binding Characteristics of Nicotinic Ligands and Their Pharmacology," *Pharmacol. Biochem. Behav.* 30(1):255–267 (May 1988).

Smith, G., "Animal Models for Alzheimer's Disease: Experimental Cholinergic Denervation," *Brain Res. Rev.* 13(2):103–118 (Apr./Jun. 1988).

Spencer, D.G., et al., "Direct Autoradiographic Determination of M1 and M2 Muscarinic Acetylcholine Receptor Distribution in the Rat Brain: Relation to Cholinergic Nuclei and Projections," *Brain Res.* 380(1):59–68 (Aug. 13, 1986).

Woodruff, G.N., et al., "Binding of [$^3$H]Sulpiride to Purified Rat Striatal Synaptic Membranes," *Neuroscience* 6(3):407–410 (1981).

Yamamura, H.I., et al., (eds), In: Neurotransmitter Receptor Binding, 2nd ed., Raven Press, New York (1985).

(R = cyclohexanemethyl)

M₂ RECEPTOR LIGAND FOR THE TREATMENT OF NEUROLOGICAL DISORDERS

This application is a continuation of Ser. No. 08/042,872, filed 5 Apr. 1997, now abandoned.

BACKGROUND OF THE INVENTION

The present invention is in the field of neural receptors, and more particularly in the area of ligands to the muscarinic₂ receptor.

Muscarinic Cholinergic Receptors

Acetylcholine triggers two classes of membrane receptors: nicotinic and muscarinic. The nicotinic receptor is a cation-specific channel in postsynaptic membranes, while the muscarinic receptor is a seven-helix transmembrane protein that triggers G proteins. Muscarinic cholinergic receptor blockade impairs memory performance, whereas enhancing muscarinic receptor activity improves memory function.

Molecular biological studies have indicated the existence of at least five subtypes of muscarinic cholinergic receptor. Bonner, T. I., *Trends Neurosci.*, 12:145–151 (1989). The messenger RNA (mRNA) associated with the synthesis of these receptor subtypes has been localized using the technique of in situ hybridization. Buckley, N. J., et al., *J. Neurosci.*, 8:4646–4652 (1989). These muscarinic receptors are widespread throughout the central nervous system (CNS), except for the M₅ receptor, which appears to be relatively specialized and found in only a few unique regions. Liao, C.-F., et al., *J. Biol. Chem.*, 264:7328–7337 (1989). The existence of muscarinic cholinergic receptor subtypes holds the promise of developing new drugs which target only one receptor while not affecting others. The many side effects of cholinergic compounds developed to date, Colleton, D., *Neurosci.*, 19(1):1–28 (1986), make this approach a very desirable one. A more specific drug which acts at only one receptor subtype would be expected to be more focused in its effects.

The Muscarinic₂ Receptor

The release of acetylcholine (ACh) appears to be modulated by presynaptic receptors of the muscarinic₂ (M₂) type. Over the past several years, evidence has accumulated that M₂ receptors are presynaptic in location at several sites in the CNS, Spencer, D. G., et al., *Brain Res.*, 380:59–68 (1986), and these sites are reduced in Alzheimer's disease. Mash, D. C., et al., *Science*, 288:1115–1117 (1985), Quirion, R., et al., *TIPS*, Dec. Suppl. 80–84 (1989). The presynaptic M₂ receptors on cholinergic neurons represent autoreceptors which regulate the release of ACh from the cholinergic neuron. Pittel, Z., et al., *J. Neurochem.*, 55:665–672 (1990). Use of a specific M₂ ligand, which would block these sites, would be expected to increase the levels of ACh at the synapse, thereby increasing the effectiveness of ACh as a neurotransmitter at the synapse and in areas where its concentration has been reduced by loss of cholinergic neurons as seen in AD. Several relatively specific M₂ antagonists have been developed. However, these antagonists do not cross the blood-brain barrier.

Neurological Disorders

Dementia

Dementia is a progressive decline in mental function, memory, and in acquired mental skills. About 11% of people in the United States over 65 years of age show mild to severe mental impairment, and from age 75 on the incidence of dementia is 2% higher with each year of life. Currently over one million people in the United States suffer serious dementia, and an estimated 120,000 of those die each year of causes related to severe dementia. Goldman, J. and Côté, L., *Principles of Neural Science*, 3rd Edition, ed. Kandel, et al., 974–983 (Elsevier New York 1991).

About 70% of all cases of dementia are due to Alzheimer's disease, while a small percentage of cases are associated with other neurodegenerative diseases, such as Huntington's disease, or Parkinson's disease.

Alzheimer's Disease

Alzheimer's Disease (AD) is characterized by cell loss in the cholinergic system, in the septohippocampal pathway, and in the projections from the nucleus basalis to the cerebral cortex, Colleton, D., *Neurosci.*, 19(1):1–28 (1986), Smith, G., *Brain Res. Rev.*, 13:103–118 (1988). The involvement of cholinergic drugs in memory function has been well documented. For example, muscarinic cholinergic antagonists such as scopolamine impair memory function. Several cholinergic agonists have been developed which affect binding at muscarinic receptor sites. Cholinergic agonists and anticholinesterases have been successfully employed to improve memory in selected patients. Colleton, D., *Neurosci.*, 19(1):1–28 (1986). These compounds, however, are short-acting and their side-effects soon become intolerable to the treated patients. Colleton, D., *Neurosci.*, 19(1):1–28 (1986).

It is therefore an object of the present invention to provide compounds useful for the treatment of neurological disorders.

It is a further object of the present invention to provide a method of treatment of neurological disorders.

It is another object of the present invention to provide compounds for the treatment of dementia that cross the blood-brain barrier in an effective, therapeutic manner, and which may be administered either orally, intravenously, or parenterally.

It is another object of the present invention to provide compounds for the treatment of dementia which minimize the side effects associated with current methods of treatment for neurological disorders, and which are suitable for long-term treatment.

SUMMARY OF THE INVENTION

Muscarinic M₂ receptor ligands are described which are suitable for the treatment of neurological disorders, and which may be administered with minimal side-effects.

The compounds described herein have the following general structures:

1st Generation M₂ Ligand

R¹, R², and R³ independently=alkyl such as methyl, isopropyl, or t-butyl; cycloalkyl such as cyclopentyl, cyclohexylmethyl, or adamantyl; arylalkyl such as benzyl, napthylmethyl, or phenylpropyl; but are not limited to these alkyl, cycloalkyl, or arylalkyl groups, and are optionally substituted with the following groups: alkyl, aryl, alkoxy, aryloxy, amino, alkylthio, arylthio, halogen, nitro, alkyl or aryl carbonyl, alkyl or aryl sulfonyl, alkyl or aryl sulfamido, alkyl or aryl carbonamido, alkyl or arylurea.

wherein n is between 1 and 20.

2nd Generation M₂ Ligand

X=1'CH, N
Y=—CONR¹—, —NR₁CO—, —CH₂NR¹, —NR¹CH₂—, —NCO(CH₂)ₙNR₁—;
R¹=alkyl, such as methyl, isopropyl, or t-butyl; cycloalkyl, such as cyclopentyl, cyclohexylmethyl, or adamantyl; arylalkyl, such as benzyl, napthylmethyl, or phenylpropyl; alkyl- or arylcarbonyl, such as cyclohexane carbonyl or benzoyl; alkyl- or aryl sulfonyl, such as methane sulfonyl or napthalenosulfonyl; alkyl- or arylurea, such as cyclohexylurea or phenylurea; but not limited to these alkyl or aryl groups and optionally substituted by the following groups: alkyl, aryl, alkoxy, aryloxy, amino, halogen, nitro, alkyl or aryl carbonyl, alkyl or aryl sulfonyl, alkyl or aryl sulfamido, alkyl or aryl carbonamido, alkyl or arylurea R² and R³=alkyl, such as methyl, isopropyl, or t-butyl; cycloalkyl, such as cyclopentyl, cyclohexylmethyl, or adamantyl; arylalkyl, such as benzyl, napthylmethyl, or phenylpropyl; but not limited to these alkyl, aryl, cycloalkyl, or arylalkyl groups, and optionally substituted with the following groups: alkyl, aryl, alkoxy, aryloxy, amino, halogen, nitro, alkylthio or arylthio, alkyl or aryl carbonyl, alkyl or aryl sulfonyl, alkyl or aryl sulfonamido, alkyl or aryl carbonamido, alkyl or arylurea.

wherein m and n is between 1 and 20.

The first-generation M₂ ligands are produced by reaction of compound 2 (FIG. 1) with an excess of a secondary amine. The secondary amine may be produced by three routes: (1) Reaction of acid chloride with N,N-dialkyl diamino alkanes, (2) reaction of a primary amine and an activated N,N-dialkyl alkanoic acid, and (3) reaction of a primary amine with a chloroalkanoyl chloride, yielding an alkylchloride, which is then reacted with a secondary amine.

Figure 1:
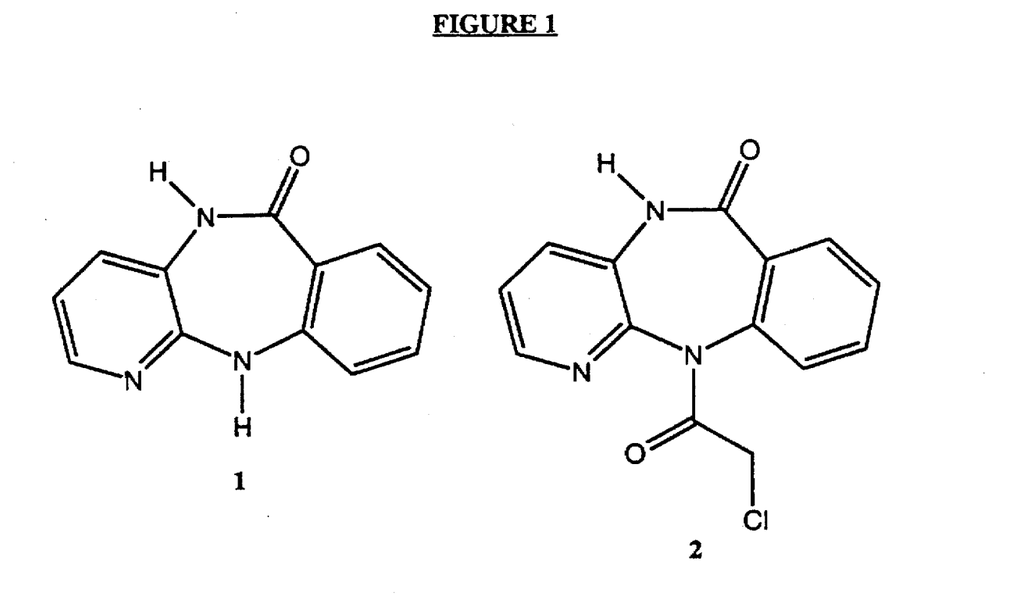
FIG. 1 are tricyclic aromatic precursors to muscarinic₂ antagonist compounds.

The second generation M₂ ligands are produced by reaction of compound 2 (FIG. 1) with secondary cycloalkylamines. The secondary cycloalkylamines may be produced by reaction of N-protected isonipecotic acid, N-benzylpiperazine, or N-benzyl-4-piperidone with the secondary amine produced in the first generation compounds. The products of these reactions are N-deprotected and reacted with compound 2 (FIG. 1).

The compounds can be administered orally, intraperitoneally, intravenously, intramuscularly, or topically in a therapeutically effective dosage, ie., producing enhancement of cognitive function with a therapeutic index of 2 or greater, most preferably orally once daily in a dosage of 10 mg compound/kg of body weight in order to enhance cognition in a subject in need of such enhancement. No toxic side effects have been observed using therapeutically effective doses. Examples demonstrate effectiveness of several compounds in standard pharmacological in vivo tests.

BRIEF DESCRIPTION OF THE DRAWINGS

FIG. 2A uses acid chloride plus diamine, followed by reduction. FIG. 2B uses amine plus dialkylamino acid, followed by reduction. FIG. 2C uses amine plus chloroalkylacid chloride, then secondary amine, followed by reduction.

DETAILED DESCRIPTION OF THE INVENTION

Muscarinic (M)₂ receptor ligands are described which are suitable for the treatment of neurological disorders, and which may be administered with minimal side-effects. A method of administration of these compounds to treat dementia is also described, as well as a method of synthesis of these compounds.

The compounds are suitable for the treatment of dementia associated with, but not limited to, the following conditions: Alzheimer's disease, Parkinson's disease, Huntington's disease, senile dementia, alcoholism, meningitis, neonatal hypoxia, stroke, or global cerebral ischemia.

Synthesis of $M_2$ Receptor Ligands

As used herein, the following definitions apply: The term "alkyl," unless otherwise defined, refers to a $C_1$ to $C_{20}$ straight or branched alkyl group, and specifically includes methyl, isopropyl, and t-butyl. The term "cycloalkyl," unless otherwise defined, refers to a cyclic alkyl group of from 3 to 10 carbon atoms; The term "alkoxy," unless otherwise defined, refers to a moiety of the structure O-alkyl; The term "aryl," unless otherwise defined, refers to a phenyl or benzyl, or substituted phenyl, or substituted benzyl, wherein the substituent is (A) alkyl, such as methyl, isopropyl, or t-butyl; (B) cycloalkyl, such as cyclopentyl, cyclohexylmethyl, or adamantyl; arylalkyl, such as benzyl, napthylmethyl, or phenylpropyl; alkyl- or arylcaronyl, such as cyclohexane carbonyl or benzoyl; alkyl- or aryl sulfonyl, such as methane sulfonyl or napthalenosulfonyl; alkyl- or arylurea, such as cyclohexlurea or phenylurea; and (C) optionally substituted with the following groups: alkyl, aryl, alkoxy, aryloxy, amino, halogen, nitro, alkyl or aryl carbonyl, alkyl or aryl sulfonyl, alkyl or aryl sulfamido, alkyl or aryl carbonamido, alkyl or arylurea.

The compounds are predicted to selectively bind to the $M_2$ receptor with an affinity in the nanomolar range, and have low toxicity. $LD_{50} > 37.5$ mg/kg, intraperitoneally and >45 mg/kg, orally). These compounds have a molecular weight range of 300–1500 grams/mol. As defined herein, the compounds that are useful for treatment of a patient are those having a therapeutic index of 2 or greater, wherein the therapeutic index is the lethal dosage $(LD)_{50}$ divided by the effective dosage $(ED)_{50}$.

The compounds are also predicted to be acid-stable, in order to make possible oral administration.

The modified compounds described herein have the following general structures:

$1^{st}$ Generation $M_2$ Ligand $R^1$, $R^2$, and $R^3$ independently=alkyl such as methyl, isopropyl, or t-butyl; cycloalkyl such as cyclopentyl, cyclohexylmethyl, or adamantyl; arylalkyl such as benzyl, napthylmethyl, or phenylpropyl; but are not limited to these alkyl, cycloalkyl, or arylalkyl groups, and are optionally substituted with the following groups: alkyl, aryl, alkoxy, aryloxy, amino, alkylthio, arylthio, halogen, nitro, alkyl or aryl carbonyl, alkyl or aryl sulfonyl, alkyl or aryl sulfamido, alkyl or aryl carbonamido, alkyl or arylurea.

wherein n is between 1 and 20.

$2^{nd}$ Generation $M_2$ Ligand

X=—CH, N
Y=—CONR$^1$—,  —NR$^1$CO—,  —CH$_2$NR$^1$—,
—NR$^1$CH$_2$—,  —NCO(CH$_2$)$_n$NR$^1$;

$R^1$=alkyl, such as methyl, isopropyl, or t-butyl; cycloalkyl, such as cyclopentyl, cyclohexylmethyl, or adamantyl; arylalkyl, such as benzyl, napthylmethyl, or phenylpropyl; alkyl- or arylcarbonyl, such as cyclohexane carbonyl or benzoyl; alkyl- or aryl sulfonyl, such as methane sulfonyl or napthalenosulfonyl; alkyl- or arylurea, such as cyclohexylurea or phenylurea; but not limited to these alkyl or aryl groups and optionally substituted by the following groups: alkyl, aryl, alkoxy, aryloxy, amino, halogen, nitro, alkyl or aryl carbonyl, alkyl or aryl sulfonyl, alkyl or aryl sulfamido, alkyl or aryl carbonamido, alkyl or arylurea $R^2$ and $R^3$=alkyl, such as methyl, isopropyl, or t-butyl; cycloalkyl, such as cyclopentyl, cyclohexylmethyl, or adamantyl; arylalkyl, such as benzyl, napthylmethyl, or phenylpropyl; but not limited to these alkyl, aryl, cycloalkyl, or arylalkyl groups, and optionally substituted with the following groups: alkyl, aryl, alkoxy, aryloxy, amino, halogen, nitro, alkylthio or arylthio, alkyl or aryl carbonyl, alkyl or aryl sulfonyl, alkyl or aryl sulfonamido, alkyl or aryl carbonamido, alkyl or arylurea.

wherein m is between 1 and 20.

Synthesis of First Generation $M_2$ Ligands

The first generation $M_2$ ligands are produced by reaction of compound 2 (FIG. 1) with an excess of a secondary amine. The secondary amine may be produced by three routes: (1) Reaction of acid chloride with N,N-dialkyl diamino alkanes, (2) reaction of a primary amine and an activated N,N-dialkyl alkanoic acid, and (3) reaction of a primary amine with a chloroalkanoyl chloride, yielding an alkylchloride, which is then reacted with a secondary amine. FIG. 2.

Synthesis of Second Generation $M_2$ Ligands

The second generation $M_2$ ligands are produced by reaction of compound 2 (FIG. 1) with secondary cycloalkylamines. The secondary cycloalkylamines may be produced by reaction of N-protected isonipecotic acid, N-benzylpiperazine, or N-benzyl-4-piperidone with the secondary amines produced in the first generation compounds. The products of these reactions are N-deprotected and reacted with compound 2 (FIG. 1).

Pharmaceutical Compositions

The compounds are administered topically, locally, or systemically, depending on the application. When administered systemically, the compound is preferably administered orally or intravenously, although it can be administered intraperitoneally, intramuscularly, or topically in an appropriate pharmaceutical carrier such as normal saline, or in tablet form. For topical application, the compound is preferably administered in an ointment or cream base, or by means of a transdermal patch. The compound can also be administered by controlled delivery devices, such as biodegradable polymers, or by inhalation, insufflation, or nasal spray. Suitable carriers are known to those skilled in the pharmaceutical area.

The compounds are administered orally, intraperitoneally, intramuscularly, subcutaneously, or topically in a therapeutically effective dosage to enhance cognition or otherwise alleviate the symptoms of the neurological disorder. In the most preferred embodiment, the compounds are administered orally once daily in a dosage range equivalent to 10 mg/kg. For mice, the $LD_{50}$ for oral administration is 45 mg/kg, and the $LD_{50}$ for intraperitoneal administration is 37.5 mg/kg. Only those compounds having a therapeutic index of 2 or greater are administered to a patient.

The concentration of active compound in the drug composition will depend on absorption, inactivation, and excretion rates of the drug as well as other factors known to those skilled in the art. It is to be noted that dosage values will also vary with the condition of the subject being treated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

For oral delivery, the compounds may be enclosed in capsules, compressed into tablets, microencapsulated, entrapped in liposomes, in solution or suspension, alone or in combination with a substrate-immobilizing material such as starch or poorly absorbable salts such as immodium. Pharmaceutically compatible binding agents can be included as part of the composition. The tablets or capsules may contain, for example, any of the following ingredients, or compounds of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate or Sterores; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier. In addition, dosage unit forms can contain various other materials which modify the physical form of the dosage unit, for example, coatings of sugar, shellac, or other enteric agents.

The present invention will be further understood with reference to the following non-limiting examples.

EXAMPLE 1

Synthesis of $M_2$ Receptor Ligands

The compounds described herein have a tricyclic aromatic ring system. The tricyclic aromatic ring system is attached to an amine-containing side-chain via an acetyl group. The tricyclic aromatic 5,11-dihydro-6H-pyrido [2,3-b][1,4]-benzodiazepin-6-one, 1 and its chloroacetyl derivative 5,11-dihydro-11-(chloroacetyl)-6H-pyridol[2,3-b][1,4]-benzodiazepin-6-one, 2 were prepared according to standard procedures and had physical and spectroscopic properties identical to the reported values (Engel, W. W., et al., *J. Med. Chem.*, 32:1718–1724 (1989); U.S. Pat. No. 3,406,168, 1968). The chloroacetyl derivative 2, was used in all of the syntheses. See FIG. 1 for structures.

a. First Generation $M_2$ Ligands

The first $M_2$ ligands produced have the general structure shown in the formula described above. They were produced in 65–85% yield by reaction of the acetyl chloride 2 with an excess of a secondary amine. The secondary amines can be produced via three routes, all proceeding through an amide which is reduced in the final step to yield the secondary amine, as shown by FIG. 2.

Figure 2A:
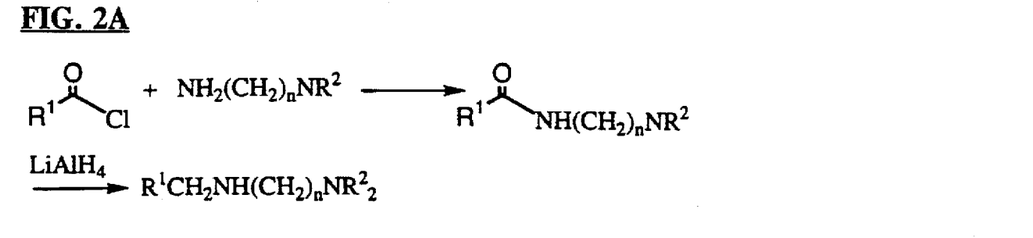
FIGS. 2A, 2B, and 2C are schematics of three routes to the synthesis of secondary amines used in the synthesis of muscarinic₂ antagonist compounds.
Figure 2B:
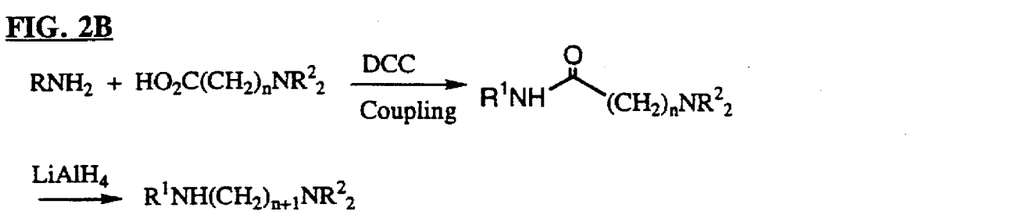
Figure 2C:
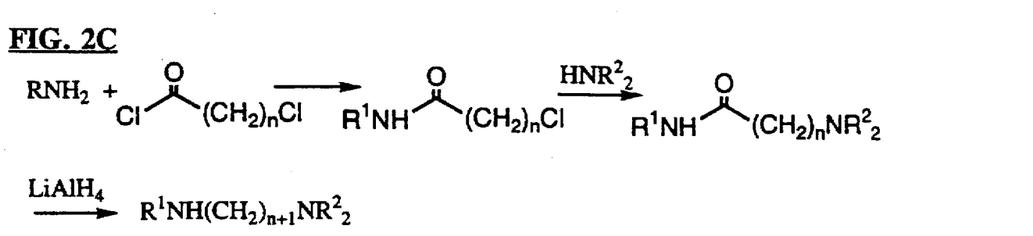

The first route, shown in FIG. 2A, involves the reaction of acid chlorides with N,N-dialkyl diamino alkanes. The second route, shown in FIG. 2B, involves the reaction of a primary amine and an activated N,N-dialkyl alkanoic acid. N,N-Dicyclohexylcarbodiimide or some other agent known to those skilled in the art could be used to activate the acid to nucleophilic attack by the amine. In the third route, shown in FIG. 2C, a primary amine is reacted with a chloroalkanoyl chloride giving an alkylchloride which is then reacted with a secondary amine such as diethylamine to produce the desired amide.

All reagents used in the secondary amine synthesis are readily available from Aldrich Chemical Co., Inc., Milwaukee, Wis.

Synthesis

The synthesis of PDC 008.004 and related compounds is shown in FIGS. 4A–4D.

N-[2-Diethylamino)ethyl]-cyclohexane carboxamide; 3: Cyclohexane carbonyl chloride (55.9 mmol) was dissolved with stirring in 650 mL acetone in a one-liter three-necked round-bottomed flask. Anhydrous potassium carbonate (55.9 mmol) was added to the flask in one portion. A condenser, 125 mL addition funnel and stopper was placed in each of the three necks. N,N-diethyl ethylenediamine (43.0 mmol) was dissolved in 100 mL acetone and transferred to the addition funnel. While the reaction mixture was stirred at 25° C., the amine/acetone solution was added over a 1.6 hour period. After 19 hours reaction at 25° C., all of the cyclohexane carbonylchloride was consumed producing a new spot by thin-layer chromatography at $R_F$ 0.25 (silica gel GF, 250 µm, 1:9:90 ammonium hydroxide:methanol:chloroform, iodine visualization). Solids were filtered and washed with acetone and the acetone was evaporated on a rotary evaporator. The residue was dissolved in 200 mL chloroform and extracted with three 100 mL portions of 10% aqueous sodium bicarbonate. The combined bicarbonate washes were back-extracted with 300 mL chloroform and the combined chloroform layers were washed with 100 mL distilled water. The chloroform was evaporated and residual solvent was removed under vacuum with gentle heating, yielding off-white crystals. Recrystallization from hexanes and ethyl acetate gave white crystals which had a melting point of 105°–107° C. (30.9 mmol, 72% yield). Spectroscopic properties were consistent with the proposed structure.

N-[2-(diethylamino)ethyl]cyclohexanemethyl amine, 4: Compound 3 (11.2 mmol) was dissolved in 150 mL diethyl ether in a 250 mL flask which was purged with argon. Lithium aluminum hydride (16.8 mmol, 1.0M in diethyl ether) was added in one portion via a gas-tight syringe. After one hour, compound 3 ($R_f$ 0.5) is completely consumed producing one new spot at $R_f$ 0.4 (silica gel GF, 250 µm, 1:9:90 ammonium hydroxide:methanol:chloroform). To quench any remaining hydride, 0.65 mL water was added with stirring, then 0.65 mL 15% aqueous sodium hydroxide, then 1.95 mL water. The white precipitate was filtered and washed with 100 mL diethyl ether. The ether was dried over sodium sulfate and evaporated with only gentle heating on a rotary evaporator. A clear colorless liquid was obtained (9.05 mmol, 81% yield) which had spectroscopic properties consistent with the proposed structure.

PDC 008.004, 5: To a 500 mL round-bottomed flask containing a stirbar was added 4.41 mmol 2, 7.06 mmol 4, 7.06 mmol sodium carbonate and 170 mL acetonitrile. Not all of 2 was soluble at 25° C. Upon heating to reflux (90° C.), all solids dissolve. After 22 hours, thin layer chromatography (silica gel GF, 250 µm, 1:9:90 ammonium hydroxide:methanol:chloroform) shows that 2 ($R_f$ 0.5, ultraviolet and iodine, active) is completely consumed producing a new spot at $R_f$ 0.2 (ultraviolet and iodine active). Some unreacted 4 ($R_f$ 0.4, iodine active) is still present. As the solution cools to room temperature, white solids precipitate from acetonitrile. The sodium carbonate is filtered and washed with acetonitrile. The solvent is evaporated and recrystallized from acetonitrile to obtain white needle-like crystals With a melting point of 208°–209° C. (3.77 mmol, 86% yield). This material had spectroscopic properties consistent with the proposed structure. The extinction coefficient at 285 nm in 1-octanol is $8199\pm616 M^{-1}cm^{-1}$. The partition coefficient (log P) between 1-octanol and 0.1M phosphate is $0.78\pm0.18$.

11-[[[2-(Diethylamino)ethyl]cyclohexylmethylamino]-acetyl]-5,11-dihydro-6H-pyrido [2,3-b][1,4]-benzodiazepin-6-one hydrochloride salt, 6: Compound 5 (1.29 mmol) was converted to its hydrochloride salt by dissolving it in absolute ethanol saturated with anhydrous hydrogen chloride until the pH of the solution was less than 2 (approximately 10 mL). The salt was crystallized by adding 100 mL anhydrous diethyl ether to the boiling ethanolic solution. The white powdery solids which formed were filtered and washed with two 50 mL portions of ether. This procedure was repeated and a fine white powder was obtained which decomposed at 190° C. before it melted (1.22 mmol, 94% yield). The white solid had physical and spectroscopic properties consistent with the proposed structure. The extinction coefficient at 281 nm in 0.1M phosphate is $9060 M^{-1}cm^{-1}$. The partition coefficient (log P) between 0.1M phosphate and 1-octanol is 0.16.

b. Synthesis of Related Compounds

11-[[[2-(Diethylamino)ethyl]amino]-acetyl]-5,11-dihydro-6H-pyrido [2,3-b][1,4]-benzodiazepin-6-one, 7: N,N-diethylethylenediamine (10.7 mmol) and 2 (3.52 mmol) were dissolved in 200 mL acetonitrile containing sodium carbonate (5.22 mmol) and a stirbar. The mixture was refluxed for 18 hours at 95° C. Thin-layer chromatography (silica gel GF, 250 µm, 1:9:90 ammonium hydroxide: methanol: chloroform) showed almost complete consumption of 2 ($R_f$ 0.55, UV and iodine active), the presence of some N,N-diethyl ethylenediamine ($R_f$ 0.1, iodine active) and a new major spot at $R_f$ 0.45 (UV and iodine active). Solids were filtered from the reaction mixture and washed with acetonitrile. The solvent was evaporated and the residue was dissolved in ethyl acetate and 10% aqueous sodium bicarbonate. 125 mL ethyl acetate solution was washed with three 50 mL portions 10% aqueous bicarbonate. Bicarbonate was back extracted with ethylacetate (75 mL), combine organics and wash with 100 mL distilled water. The ethyl acetate solution was dried over sodium sulfate, filter and evaporate solvent. The residue obtained was recrystallized from ethanol and water to yield an off-white solid with a melting point of 96°–97° C. (0.206 mmol, 6% yield). The physical and spectroscopic properties were consistent with the proposed structure.

N-[2-(diethylamino)ethyl]-5-dimethylamino-1-napthalene sulfonamide, 8: 5-Dimethylamino-1-napthalenesulfonylchloride, DANSYL chloride (0.56 mmol) was dissolved in 5 mL acetone with stirring at 25° C. Anhydrous potassium carbonate (0.56 mmol) was added in one portion and N,N-diethyl ethylenediamine (0.43 mmol) in 3 mL acetone was added over a five minute period from an additional funnel. After 18 hours at 26° C., thin-layer chromatography (silica gel GF, 250 µm, 1:9:90 ammonium hydroxide: methanol: chloroform) showed some N,N-diethyl ethylenediamine ($R_f$ 0.25, iodine active), some DANSYL chloride ($R_f$ 0.0, UV active) and a major new fluorescent yellow spot at $R_f$ 0.65 (iodine and UV active). Solids were filtered and washed with acetone and the acetone was evaporated. The fluorescent spot at $R_f$ 0.65 was isolated by preparative thin layer chromatography (silica gel G, 1000 µm, 1:9:90 ammonium hydroxide: methanol: chloroform). The largest band at $R_f$ 0.45–0.65 was removed from the silica with 250 mL ethylacetate. The ethylacetate was washed with 100 mL water and dried over sodium sulfate. Evaporation of the solvent gave a yellow-green film (0.210 mmol, 49% yield) which had a proton NMR spectrum consistent with the proposed structure.

c. Second Generation $M_2$ Ligands

The second generation $M_2$ ligands have the general structure described above. Like the first generation ligands, they have a tricyclic aromatic ring system linked via an acetyl group to the amine-containing sidechain. However, a small aliphatic ring has been incorporated in the sidechain in between the terminal amine and the aromatic 1. The amide and amine functionality in the linker were chosen to allow the facile synthesis of a wide variety of linkers of varying chain length and physical and chemical properties. The nature of the terminal amine can also be varied, if desired.

The synthesis of the sidechains can be effected in a few steps from the readily available starting materials shown in Table 2. Aldrich Chemical Co., Inc., Milwaukee, Wis. These precursors are shown only to demonstrate the wide variety of options available in the synthesis and they should not be taken as a complete list. Methods for coupling the various constituents of the sidechain together are known to those skilled in the art.

TABLE 2

| RING SYSTEM | LINKERS | LIPOPHILIC SUBSTITUENTS |
|---|---|---|
| Bz-N-piperidine-ketone | Cl-CO-(CH$_2$)$_n$Cl | R$^1$-CO-Cl |
| H-N-piperidine-CO$_2$H | HO-CO-(CH$_2$)$_n$NR$^1_2$ | R$^1$SO$_2$Cl |
| H-N-piperidine-NH$_2$ | NH$_2$(CH$_2$)$_n$NR$^1_2$ | R$^1$NCO |
| H-N-piperidine-NH-H | Cl(CH$_2$)$_n$NR$^1_2$ | R$^1$NCS |
| H-N-piperidine-CH$_2$OH | | R$^1$X |
| | | TERMINAL AMINE |
| | | HNR$^2$R$^3$ |

Bz = benzoxy

The ring system could come from the substituted piperidines or piperazine in the protected or unprotected forms. The linker is available, for example, from varying lengths of the diethyl amino alkanoic acids, the N,N-dialkyl diamines or the N,N-dialkyl alkylchlorides. In the aforementioned cases, these also incorporate the terminal amine and they are available in limited choices for R$^1$ such as ethyl, methyl, etc. For more flexibility, the chloroalkyl acid chlorides provide a means of varying the chain length and adding the desired secondary amine in another step. The wide range of secondary amines available makes this an attractive route. There are a large variety of alkyl and aryl groups readily available as the acid chloride, sulfonyl chloride, alkyl halide, isocyanate and isothiocyanate which are easily attached and could alter the properties of the ligands. Desirable properties which could be achieved through attachment of such active groups are listed as examples, but are not limited to the following: the ability to fluoresce, the presence of radioactive isotopes, changes in polarity, active groups for irreversible ligand binding (photoaffinity labelling), and fluorine-containing substituents for NMR imaging.

Synthesis

Figure 3:
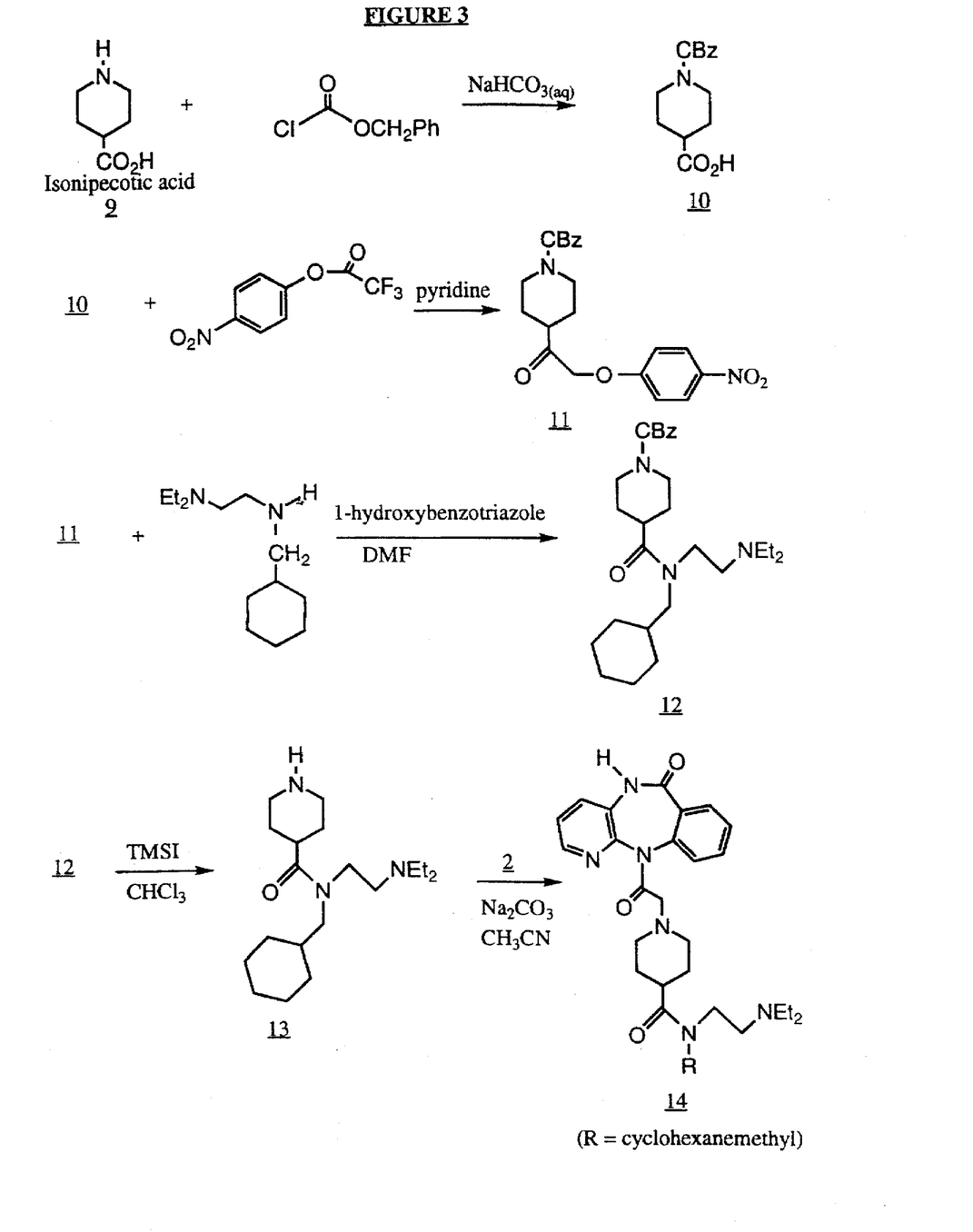
FIG. 3 is a schematic of the syntheses of second generation muscarinic₂ compounds.
Figure 4A:
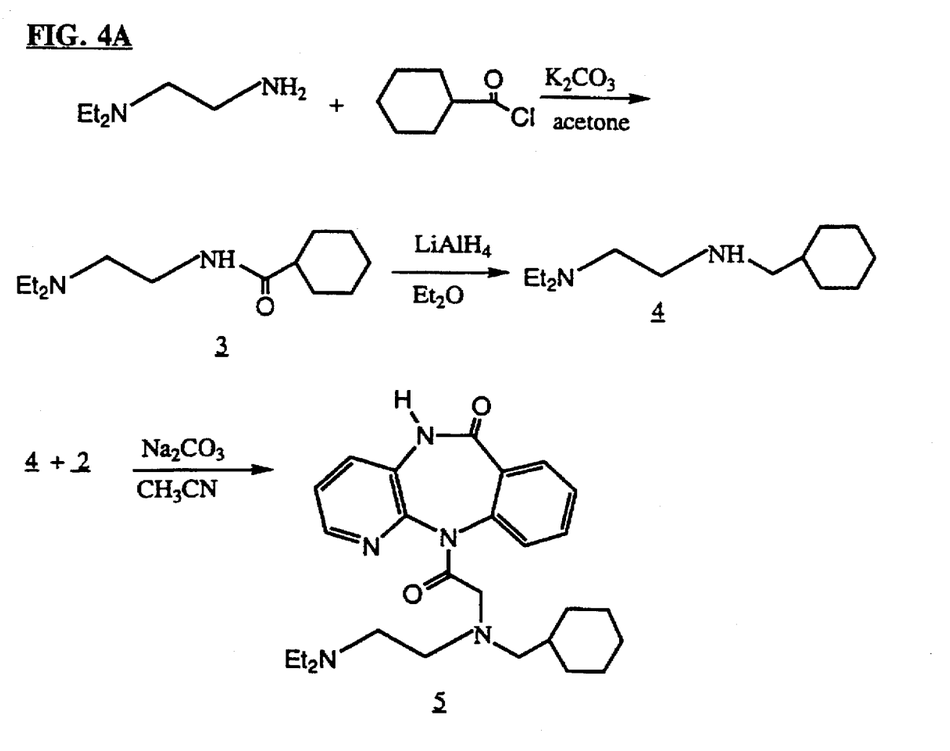
FIGS. 4A, 4B, 4C and 4D depict one embodiment of the synthesis of 11-[[[2-(diethylamino)ethyl] cyclohexylmethylamino]-acetyl]-5,11-dihydro-6H-pyrido [2,3-b][1,4]-benzodiazepin-6-one (PDC 008.004).
Figure 4B:
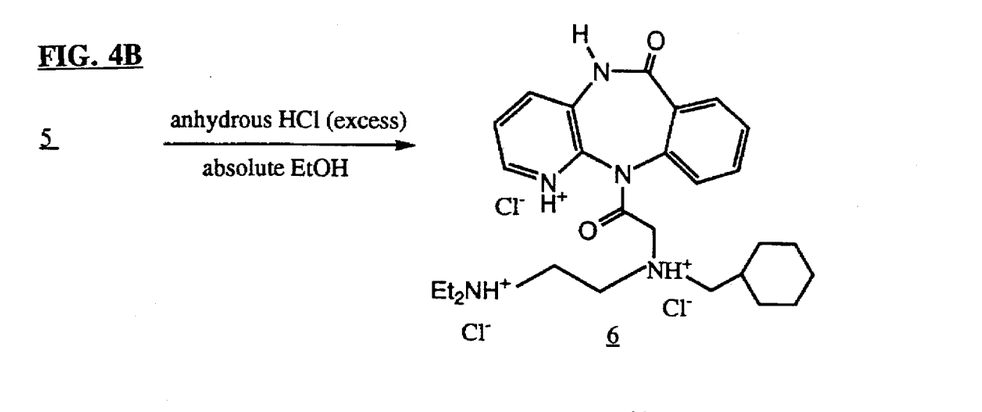
Figure 4C:
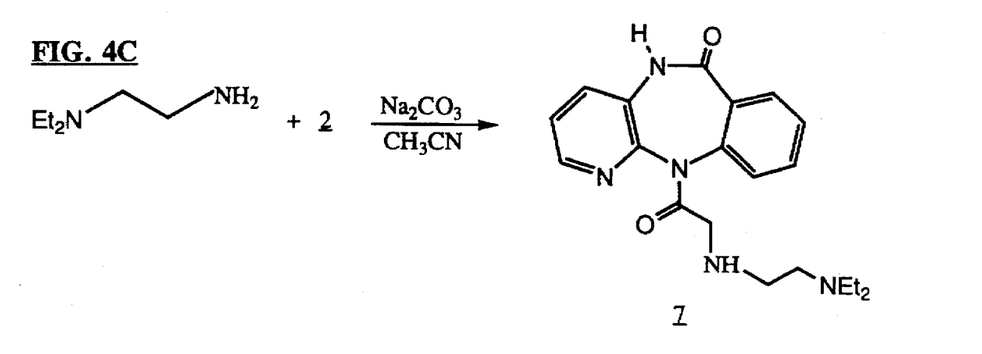
Figure 4D:
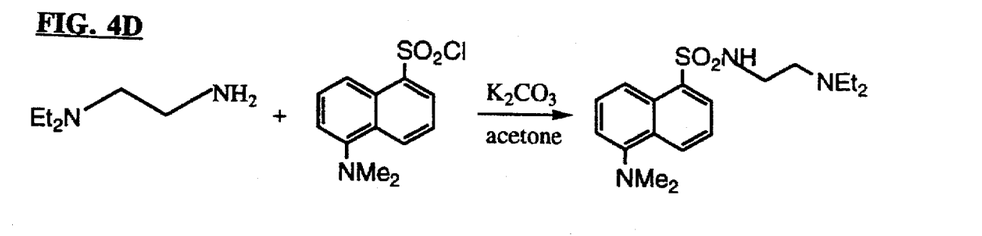

FIG. 3 shows the synthesis of the second generation M$_2$ ligands starting from isonipecotic acid, 9. Aldrich Chemical Co., Inc., Milwaukee, Wis. The amino function is protected, the acid is activated to nucleophilic attack, reacted with the secondary amines produced for the first generation compounds (4, for example), deprotected and reacted with the acetyl chloride derivative of the tricyclic aromatic, 2 giving the desired compounds.

1-Benzyloxycarbonyl-4-piperidinecarboxylic acid, 10: Compound 10 was prepared from isonipecotic acid, 9 using a literature procedure (*Chemistry of the Amino Acids*, Vol. 2, John Wiley and Sons, Inc., pp. 891–895 (New York 1961)). Isonipecotic acid (7.74 mmol) was dissolved in 16 mL 10% aqueous sodium bicarbonate (19.3 mmol) with stirring. Benzylchloroformate (8.52 mmol) was added in five portions over a thirty minute period. The reaction mixture was stirred vigorously to effectively mix the benzylchloroformate with the aqueous solution. The mixture was stirred 18 hours at 25° C., at which time 10 mL water was added in an attempt to dissolve the cloudy white solids. The aqueous solution was washed with 50 mL diethyl ether, neutralized to pH3 with 5N hydrochloric acid, and washed with two 30 mL portions of ethyl acetate. The ethyl acetate was dried over sodium sulfate, filtered and evaporated yielding a clear, colorless, viscous oil (7.6 mmol, 98% yield). Thin layer chromatography (silica gel GF, 250 μm, 4:1:1 1-butanol: acetic acid: water), showed no starting material present (R$_f$ 0.25, UV active), and only one spot at R$_f$ 0.85 which is both UV and iodine active. The physical and spectroscopic properties of this oil are consistent with the structure proposed.

4-Nitrophenyl-1-benzyloxycarbonyl-4-piperidinecarboxylate, 11: Compound 11 was produced from 10 using a literature procedure involving 4-nitrophenyl trifluoroacetate (Sakahibara, S. and Innhai, N., *Bull. Chim, Soc. Jpn.*, 37:1231–1232 (1964)). Compound 10 (5.7 mmol) was dissolved in 4 mL pyridine with stirring. As soon as 4-nitrophenyl trifluoroacetate (5.7 mmol) was added, a yellow color developed. The reaction mixture was stirred for 20 hours at 25° C. at which time thin layer chromatography (silica gel GF, 250 μm, 1:9:90 ammonium hydroxide:methanol:water) showed starting material 10 was almost completely consumed (R$_f$ 0.1, UV and iodine active) producing a new major spot at R$_f$ 0.9 which was both UV and iodine active. The reaction mixture was dissolved in 150 mL diethyl ether and washed with two 150 mL portions 10% aqueous copper sulfate to remove pyridine, eight 100 mL portions 10% aqueous sodium bicarbonate to remove 4-nitrophenol and two 100 mL portions of water. The diethyl ether was evaporated leaving a clear, colorless oil which formed an off-white solid upon cooling in a −20° C. freezer. This sample was recrystallized from hexanes and ethyl acetate. The physical and spectroscopic properties were consistent with the structure assigned.

N-[2-(Diethylamino)ethyl]-N-cyclohexanemethyl 1-benzyloxycarbonyl-4-piperidinecarboxamide, 12: Compound 12 was prepared by the reaction of 4 with the activated ester 11 in the presence of 1-hydroxybenzotriazole (Glass, J. G. and Pelzig, M. *Int. J. Peptide Protein Res.*, 12:75–80 (1978)). To a solution of compound 4 (1 mmol) and 1-hydroxybenzotriazole (1 mmol) in 1 mL dimethylformamide was added the nitrophenyl ester, 11 (1 mmol). After 1 hour at 25° C., the reaction was diluted with 10 mL diethyl ether. A precipitate formed which was washed with diethyl ether, cold water and dissolved in hot water. On standing and cooling to room temperature an off-white solid formed. Physical and spectroscopic properties were consistent with the proposed structure.

N-[2-(Diethylamino)ethyl]-N-cyclohexane methyl 4-piperidine carboxamide, 13: Deprotection of the benzyoxylcarbonyl protected piperidine was effected using trimethylsilyl iodide, TMSI (Lott, R. S., et al., *J.C.S. Chem. Commun.*, 495–496 (1979)). To a solution of 12 (0.1 mmol) in 1 mL chloroform was added TMSI (0.12 mmol) via a dry gas-tight syringe. The solution was heated to 50° C. for 10 minutes at which time methanol (0.4 mmol) was added via a syringe to quench the reaction. Once the reaction mixture cooled to room temperature, the solvent was evaporated and the residue recrystallized from ethyl acetate and hexanes to yield an off-white solid. The physical and spectroscopic properties were consistent with the proposed structure.

11-[[N-[2-(Diethylamino)ethyl]-N-cyclohexanemethyl 1-piperidine-4-carboxamido]-acetyl]-5,11-dihydro-6H-pyrido[2,3-b][1,4]-benzodiazepin-6-one, 14: To a solution of 13 (1.6 mmol) in 40 mL acetonitrile was added 2 (1.0 mmol) and sodium carbonate (1.6 mmol). The solution was heated to reflux for 18 hours. The solution was cooled to room temperature, the solids filtered and washed with acetonitrile and the solvent evaporated. The off-white solids obtained were recrystallized from acetonitrile. The white flaky solid obtained had physical and spectroscopic properties consistent with the proposed structure.

The following compounds were synthesized by similar methods to those described above.

R = H

R = —CH$_2$(CH$_2$)$_{13}$CH$_3$

EXAMPLE 2

Figure 5:
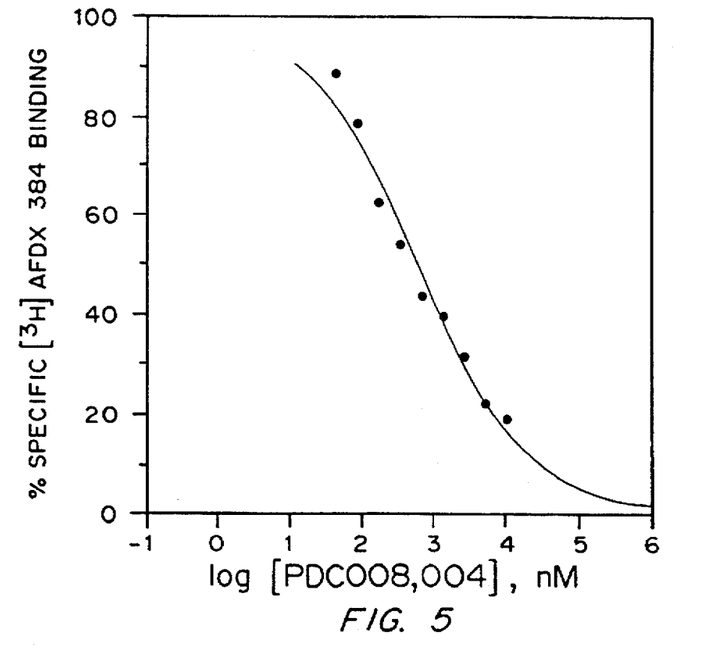
FIG. 5 is a graph of the inhibition of [³H]AF-DX-384 binding to M₂ receptors in the rat brain by PDC008.004, determined as % specific [³H]AFDX 384 binding versus log [PDC008.004] in nM.

Biochemical Pharmacology of 11-[[[2 (diethylamino)ethyl]cyclohexylmethylamino]-acetyl]- 5,11-dihydro-6H-pyrido [2,3-b][1,4]-benzodiazepin-6-one Studies examining inhibition of [$^3$H]AF-DX-384 binding to M$_2$ receptors in the rat brain by PDC 008.004(FIGS. 4A–4D), have yielded an Ki of 422 nM (FIG. 5). These results indicate that this compound has an affinity for M$_2$ receptors in the nanomolar range. Thus, compounds having an affinity in the nanomolar range most likely possess therapeutic effectiveness.

EXAMPLE 3

Evaluation of 11-[[[2-(diethylamino)ethyl] cyclohexylmethylamino]-acetyl]-5,11-dihydro-6H-pyrido [2,3-b][1,4]-benzodiazepin-6-one in Watermaze Behavioral Studies The following procedures are standard techniques routinely used by those skilled in the art (Morris, R. G. M., 1981)

Materials

1. ANIMALS

Male C$_{57}$BL/6 mice, 30 g body weight. Minimum 50 animals. Obtainable from The Jackson Laboratories, Bar Harbor, Rt. 3, Me. 04609.

The animals need at least one week of acclimatization to the colony prior to experiments. Housing: standard environment but as quiet as possible.

2. EQUIPMENT

2A. Water Tank and Accessories

Circular water tank made of sturdy (10 mm thick, minimum) black (or very dark, opaque) lucite or other plastic. Diameter of the tank: 1 meter; Wall height: 50 cm. The tank must have a valve connected to a large diameter (min 1.5 cm inner) water filling/draining rubber hose (min. length 10 ft).

2B. Targets

Two targets, one made of the same plastic as the water tank (the "black target"), and one made of translucent variety. Base made of heavy lucite (1 inch thick) shaped as a square with 10 inch sides. Height between the upper surface of the base and the lower surface of the target platform: 20 cm. Target platform support: 20 cm tall, circular rod (1 inch diam.). Circular target platform, 8 cm across, made of 0.5 cm thick plastic and covered with a non-skid material (surgical tape can be used) painted either black or white (depending on the target).

Target cues: White sheets, either to be suspended above the rim of the tank wall or from the rim of the tank wall, and which depict easily recognizable patterns.

A supply of powdered skim milk to cloud the water in the tank. Tank cleaning supplies (Alconox, sponges, etc.)

2B. Data Collecting Equipment

A standard personal computer with hard disk and 3.5 floppy inch drives, monitor and keyboard on a movable stand. The computer should be devoted to the study during its duration.

WATERMAZ© data collecting program Infallible Software, Inc., Durham, N.C.).

Statistics software.

3. Environment

The water tank was placed in a space with access to a sink and both cold and hot water taps. The tank was accessible from two sides. The space was provided by a quiet, isolated room with lockable door and not too bright fluorescent ceiling illumination. The room had a stable temperature of approximately 22° C.

4. Methods

4A. Regimens

Regimen "A" consists of concurrent injections of either drug(s) or saline and swimming. Injections administered in a sequence: injection—24h—swim—2h—injection—24h—swim—2h—injection . . . etc., until a stable "time to target" plateau among the controls will be reached. If desired, this regimen can be extended for a period of additional 5-7 days to observe whether the data in the treated group(s) will eventually change with respect to controls.

Regimen "B" consists of saline or drug injected animals with agents administered for 7 days prior to swimming, followed by one day injection free (washout period) and training to target until a stable control plateau is reached.

Mice exhaust rather rapidly. Therefore, unless absolutely necessary, "mass trials" (i.e., more than one trial a day) are not advised because physical stress factor may be inadvertently introduced. Single trial/day eliminates the problem.

Ten animals/group provides sufficiently high statistical reliability. However, training of more than 40 animals/day (i.e., four groups) is impractical because of interruptions necessary for refilling the tank with fresh water, injection sequence problems, and of a vast amount of generated data that will subsequently reduce the efficiency of statistical analysis (some programs may not accept very large such numbers of data entries). Course of the experiment and data collected:

The experiments were conducted in the following sequence: Time to submerged target (7 days)—free swim [target removed (1 day)]—time to submerged target (7 days)—free swim (1 day) . . . etc. (until plateau)—reversed target [target in new position (until plateau, typically 3-5 days]—visible (black target, until plateau). Maximum time to target allowed: 120 sec. Maximum time in tank during the free swim: 60 sec.

Data: Time to target
Quadrant preference (time/quadrant)
Immobility
Number of center crossings
Movement pattern

Watermaze Behavioral Studies

Figure 6:
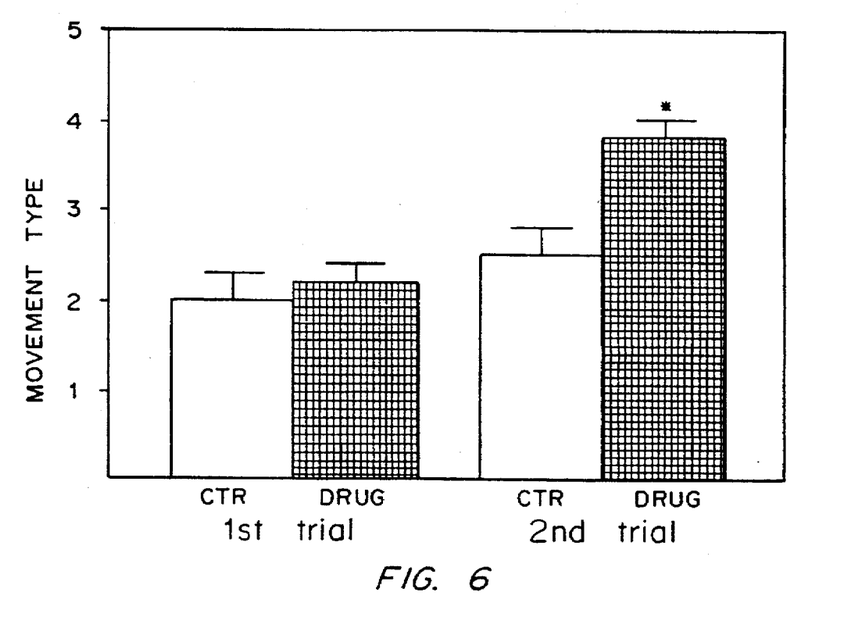
FIG. 6 is a graph of the average movement pattern changes in PDC 008.004 treated mice and in untreated (control) mice in a watermaze. Movement type: 1, wall hug; 2, wall/cross; 3, cross; 4, cross/goal; and 5, goal.
Figure 7:
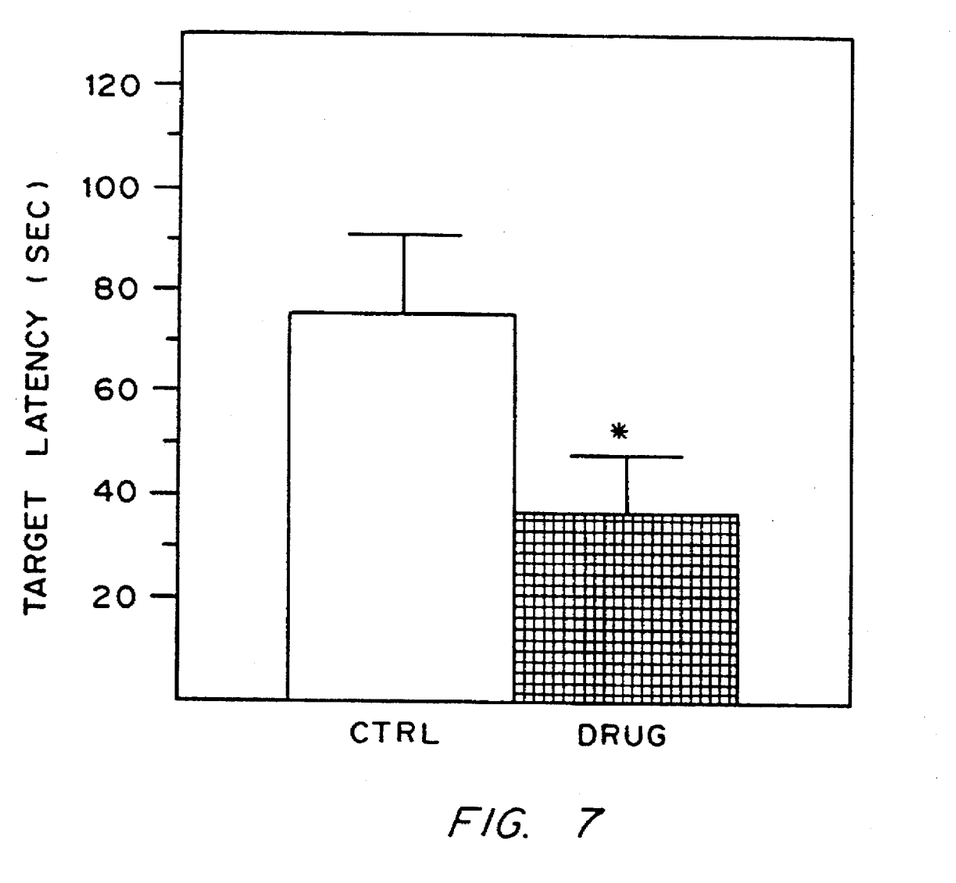
FIG. 7 is a graph of target latencies after the fourth trial in PDC 008.004 treated mice and untreated (control) mice in a watermaze.

The results are shown in FIGS. 6 and 7. The results are for 10 control animals treated intraperitoneally with 10 mg/kg vehicle, and 10 animals treated intraperitoneally with 10 mg/kg $PDC_{008.004}$. FIG. 7 indicates a substantial and significant (P>0.01) movement pattern change in the drug (11-[[[2-(diethylamino)ethyl]cyclohexylmethylamino]-acetyl]-5,11-dihydro-6H-pyrido [2,3-b][1,4]-benzodiazepin-6-one) treated mice consisting of a rapid shift from thygmotactic (wall-hugging) to center crossing and center crossing-goal oriented behavior. This behavior is consistent with increased motor activity seen after a single injection of the drug (10 mg/kg, intraperitoneally) followed by a 24 hour period prior to behavioral testing. In the control group, a slow shift from thygmotaxy to thygmotaxy/center crossing is evident, however, wall hugging is predominant. Behavior of the controls is consistent with that of saline-injected animals observed in several previous studies. Morris, R. G. M., *Learning and Motivation*, 1981.

FIG. 7 indicates a substantial statistically significant (P<0.05) decrease in the time required to find a hidden target after the fourth trial using mice treated with daily injections of PDC 008.004 (10 mg/kg, intraperitoneally).

These results indicate that the observed effects are directly related to central effects of $M_2$ receptors by the administered agent, PDC 008.004 (10 mg/kg, intraperitoneally, daily). Moreover, the presence of dyskinesia, ataxia, and absence of flaccid paralysis observed in animals injected with the drug at 100 mg/kg intraperitoneally, supports this conclusion. The very swift central cholineric mediated events) demonstrates rapid penetration into the intracerebral space.

In conclusion, the results obtained during four behavioral trials demonstrate the potential therapeutic applications of the agent, PDC 008.004, and its related compounds, in acute and chronic disorders in which cognitive processes are severely affected. Examples of such disorders are: stroke, global cerebral ischemia (after cardiac arrest), Alzheimer's, and related disorders of advanced age (i.e., senile dementia), Parkinson's and Huntington's diseases, chronic addictive disorders (i.e., alcoholism), and inflammatory disorders of the brain (i.e., meningitis). Neonatal hypoxia and related cognitive deficits may also be amenable to such treatment.

Modifications and variations of the present invention will be obvious to those skilled in the art from the foregoing detailed description. Such modifications and variations are intended to come within the scope of the appended claims.

We claim:

1. A compound having a formula selected from the group consisting of:

1st Generation M₂ Ligand

$R^1$, $R^2$, and $R^3$ are independently
a) substituted or unsubstituted $C_1$ to $C_{20}$ branched or straight chain alkyl,
b) substituted or unsubstituted $C_3$ to $C_{10}$ cycloalkyl, or
c) substituted or unsubstituted $C_1$ to $C_{20}$ branched or straight chain arylalkyl, wherein the substituted alkyl, cycloalkyl, and arylalkyl, are substituted with substituents selected from the group consisting of $C_1$ to $C_{20}$ branched or straight chain alkyl, aryl, $C_1$ to $C_{20}$ branched or straight chain alkoxy, aryloxy, amino, $C_1$ to $C_{20}$ branched or straight chain alkythio, arylthio, halogen, nitro, $C_1$ to $C_{20}$ branched or straight chain alkyl carbonamido, aryl carbonamido, $C_1$ to $C_{20}$ branched or straight chain alkylurea, and arylurea, wherein n is between 1 and 20; and 2nd Generation M₂ Ligand X is —CH or —N;
Y is —CONR¹—, —NR¹CO—, —CH₂NR¹—, —NR¹CH₂—, or —NCO(CH₂)ₙNR¹—;
$R^1$ is
a) substituted or unsubstituted $C_1$ to $C_{20}$ branched or straight chain alkyl,
b) substituted or unsubstituted $C_3$ to $C_{10}$ cycloalkyl,
c) substituted or unsubstituted $C_1$ to $C_{20}$ branched or straight chain arylalkyl,
d) substituted or unsubstituted $C_1$ to $C_{20}$ branched or straight chain alkyl carbonyl,
e) substituted or unsubstituted aryl carbonyl,
f) substituted or unsubstituted $C_1$ to $C_{20}$ branched or straight chain alkyl sulfonyl,
g) substituted or unsubstituted aryl sulfonyl,
f) substituted or unsubstituted $C_1$ to $C_{20}$ branched or straight chain alkylurea, or
g) substituted or unsubstituted arylurea, wherein the substituted alkyl, cycloalkyl, arylalkyl, alkyl carbonyl, aryl carbonyl, alkyl sulfonyl, aryl sulfonyl, alkylurea, and arylurea, are substituted with substituents selected from the group consisting of $C_1$ to $C_{20}$ branched or straight chain alkyl, aryl, $C_1$ to $C_{20}$ branched or straight chain alkoxy, aryloxy, amino, halogen, nitro, $C_1$ to $C_{20}$ branched or straight chain alkyl carbonyl, aryl carbonyl, $C_1$ to $C_{20}$ branched or straight chain alkyl sulfonyl, aryl sulfonyl, $C_1$ to $C_{20}$ branched or straight chain alkyl sulfamido, aryl sulfamido, $C_1$ to $C_{20}$ branched or straight chain alkyl carbonamido, aryl carbonamido, $C_1$ to $C_{20}$ branched or straight chain alkylurea, and arylurea;

$R^2$ and $R^3$ are independently
a) substituted or unsubstituted $C_1$ to $C_{20}$ branched or straight chain alkyl,
b) substituted or unsubstituted $C_3$ to $C_{10}$ cycloalkyl, or
c) substituted or unsubstituted $C_1$ to $C_{20}$ branched or straight chain arylalkyl, wherein the substituted alkyl, cycloalkyl, and arylalkyl, are substituted with substituents selected from the group consisting of $C_1$ to $C_{20}$ branched or straight chain alkyl, aryl, $C_1$ to $C_{20}$ branched or straight chain alkoxy, aryloxy, amino, halogen, nitro, $C_1$ to $C_{20}$ branched or straight chain alkythio, arylthio, $C_1$ to $C_{20}$ branched or straight chain alkyl carbonyl, aryl carbonyl, $C_1$ to $C_{20}$ branched or straight chain alkyl sulfonyl, aryl sulfonyl, $C_1$ to $C_{20}$ branched or straight chain alkyl sulfamido, aryl sulfamido, $C_1$ to $C_{20}$ branched or straight chain alkyl carbonamido, aryl carbonamido, $C_1$ to $C_{20}$ branched or straight chain alkylurea, and arylurea;

wherein m and n are between 1 and 20.

2. The compound of claim 1 wherein $R^1$ is cyclohexylmethyl, $R^2$ is ethyl, $R^3$ is ethyl, and n is 2.

3. The compound of claim 1 further comprising a pharmaceutically acceptable carrier for administration to a patient.

4. The compound of claim 3 wherein the pharmaceutical carrier is selected from the group consisting of carriers for intravenous administration, oral administration, administration via the respiratory tract, subcutaneous administration, intramuscular administration, rectal administration, and topical administration.

5. The compound of claim 1 selected from the group consisting of

6. A method of enhancing cognition in a subject in need thereof comprising the administration to a subject in need of treatment thereof of an effective mount to enhance cognition of a compound in a pharmaceutically acceptable carrier for administration to a patient wherein the compound is selected from the group of compounds of the following formulas:

R = H

R = —CH₂(CH₂)₁₃CH₃

1st Generation M₂ Ligand $R^1$, $R^2$, and $R^3$ are independently
a) substituted or unsubstituted $C_1$ to $C_{20}$ branched or straight chain alkyl,
b) substituted or unsubstituted $C_3$ to $C_{10}$ cycloalkyl, or
c) substituted or unsubstituted $C_1$ to $C_{20}$ branched or straight chain arylalkyl, wherein the substituted alkyl, cycloalkyl, and arylalkyl, are substituted with substituents selected from the group consisting of
$C_1$ to $C_{20}$ branched or straight chain alkyl, aryl, $C_1$ to $C_{20}$ branched or straight chain alkoxy, aryloxy, amino, $C_1$ to $C_{20}$ branched or straight chain alkythio, arylthio, halogen, nitro, $C_1$ to $C_{20}$ branched or straight chain alkyl carbonamido, aryl carbonamido, $C_1$ to $C_{20}$ branched or straight chain alkylurea, and arylurea, wherein n is between 1 and 20; and 2nd Generation M₂ Ligand X is —CH or —N;
Y is —CONR¹, —NR¹CO—, —CH₂NR¹, —NR¹CH₂—, or —NCO(CH₂)ₙNR¹—;
R¹ is a) substituted or unsubstituted $C_1$ to $C_{20}$ branched or straight chain alkyl,
b) substituted or unsubstituted $C_3$ to $C_{10}$ cycloalkyl,
c) substituted or unsubstituted $C_1$ to $C_{20}$ branched or straight chain arylalkyl,
d) substituted or unsubstituted $C_1$ to $C_{20}$ branched or straight chain alkyl carbonyl,
e) substituted or unsubstituted aryl carbonyl,
f) substituted or unsubstituted $C_1$ to $C_{20}$ branched or straight chain alkyl sulfonyl,
g) substituted or unsubstituted aryl sulfonyl,
f) substituted or unsubstituted $C_1$ to $C_{20}$ branched or straight chain alkylurea, or
g) substituted or unsubstituted arylurea, wherein the substituted alkyl, cycloalkyl, arylalkyl, alkyl carbonyl, aryl carbonyl, alkyl sulfonyl, aryl sulfonyl, alkylurea, and arylurea, are substituted with substituents selected from the group consisting of $C_1$ to $C_{20}$ branched or straight chain alkyl, aryl, $C_1$ to $C_{20}$ branched or straight chain alkoxy, aryloxy, amino, halogen, nitro, $C_1$ to $C_{20}$ branched or straight chain alkyl carbonyl, aryl carbonyl, $C_1$ to $C_{20}$ branched or straight chain alkyl sulfonyl, aryl sulfonyl, $C_1$ to $C_{20}$ branched or straight chain alkyl sulfamido, aryl sulfamido, $C_1$ to $C_{20}$ branched or straight chain alkyl carbonamido, aryl carbonamido, $C_1$ to $C_{20}$ branched or straight chain alkylurea, and arylurea;

$R^2$ and $R^3$ are independently
a) substituted or unsubstituted $C_1$ to $C_{20}$ branched or straight chain alkyl,
b) substituted or unsubstituted $C_3$ to $C_{10}$ cycloalkyl, or
c) substituted or unsubstituted $C_1$ to $C_{20}$ branched or straight chain arylalkyl, wherein the substituted alkyl, cycloalkyl, and arylalkyl, are substituted with substituents selected from the group consisting of

$C_1$ to $C_{20}$ branched or straight chain alkyl, aryl, $C_1$ to $C_{20}$ branched or straight chain alkoxy, aryloxy, amino, halogen, nitro, $C_1$ to $C_{20}$ branched or straight chain alkylthio, arylthio, $C_1$ to $C_{20}$ branched or straight chain alkyl carbonyl, aryl carbonyl, $C_1$ to $C_{20}$ branched or straight chain alkyl sulfonyl, aryl sulfonyl, $C_1$ to $C_{20}$ branched or straight chain alkyl sulfamido, aryl sulfamido, $C_1$ to $C_{20}$ branched or straight chain alkyl carbonamido, aryl carbonamido, $C_1$ to $C_{20}$ branched or straight chain alkylurea, and arylurea;

wherein m and n are between 1 and 20.

7. The method of claim 5 wherein $R^1$ is cyclohexylmethyl, $R^2$ is ethyl, $R^3$ is ethyl, and n is 2.

8. The method of claim 6 wherein the pharmaceutical carrier is selected from the group consisting of carriers for intravenous administration, oral administration, administration via the respiratory tract, subcutaneous administration, intramuscular administration, rectal administration, and topical administration, further comprising administering the compound by a route appropriate for the carrier.

9. The method of claim 6 wherein the compound is selected from the group consisting of

R = H

R = —CH₂—

R = —CH₂—

R = —CH₂(CH₂)₁₃CH₃

R = —CH₂—

R = —CH₂—.

10. The method of claim 6 wherein the subject in need of cognitive enhancement suffers from a disease or disorder selected from the group consisting of Alzheimer's disease, Parkinson's disease, Huntington's disease, senile dementia, alcoholism, meningitis, neonatal hypoxia, stroke, and global cerebral ischemia.

* * * * *